United States Patent [19]

Hazen

[11] 4,240,422
[45] Dec. 23, 1980

[54] SYRINGE WITH NEEDLE AND METHOD OF ATTACHING SAME

[75] Inventor: Thomas A. Hazen, Glendale, Calif.

[73] Assignee: American Hospital Supply Corporation, Evanston, Ill.

[21] Appl. No.: 953,604

[22] Filed: Oct. 23, 1978

[51] Int. Cl.² ............................................. A61M 5/00
[52] U.S. Cl. ................................ 128/218 N; 128/221
[58] Field of Search ............... 128/218 R, 218 N, 221, 128/215, 216

[56] References Cited

U.S. PATENT DOCUMENTS

| | | | |
|---|---|---|---|
| 3,402,713 | 9/1968 | Senkowski et al. | 128/221 |
| 3,469,581 | 9/1969 | Burke | 128/221 |
| 3,507,279 | 4/1970 | Senkowski | 128/221 |
| 3,542,024 | 11/1970 | Burke | 128/221 |
| 4,027,669 | 6/1977 | Johnston et al. | 128/218 N |

Primary Examiner—John D. Yasko
Attorney, Agent, or Firm—Larry N. Barger

[57] ABSTRACT

A hypodermic syringe with a tapered adapter surrounded by an internally threaded locking sleeve. A needle hub with at least one locking ear is threaded partway onto the tapered adapter and thereafter longitudinally staked to separate pressure contact between the needle ear and thread during storage.

6 Claims, 4 Drawing Figures

SYRINGE WITH NEEDLE AND METHOD OF ATTACHING SAME

BACKGROUND

U.S. Pat. No. 4,027,669 describes a thermoplastic syringe barrel with an integral tapered adapter surrounded by an internally threaded locking sleeve. This sleeve is longitudinally slotted to aid in strip ejection from a mold during its manufacture.

Integral locking sleeves that are strip ejected are more economical to manufacture than separately molded sleeves which must be subsequently attached to a syringe barrel, as described in U.S. Pat. Nos. 3,469,581 and 3,542,024. However, the threads in such strip ejection sleeve have limited height and tapered rear surfaces to prevent substantial damage to the threads during strip ejection. Such threads have sufficient holding power to grip the needle hub's ears when assembled by a nurse or physician immediately prior to use. This is because there is no long term distorting pressure between the hub ears and threads.

Most disposable thermoplastic syringes are sold today with a needle preattached. The needle hub's ears and threads of the locking sleeve may be in high pressure abutment for several months during shipping, storage, etc. prior to use. This can cause some relief in the holding power of the threads on the needle hub ears.

In addition, strip ejected screw threads of limited holding power have problems with machine assembly of the needle to the syringe. If the needle is longitudinally jammed (without screwing) onto the tapered adapter to snap the hub's ears behind the threads, this causes some damage to the threads, reducing their already limited holding power. Machine assembly of the needle to the syringe with a screwing motion to firmly seat the needle on the tapered adapter sometimes causes the hub ears to snap out from behind the threads and form a scar or damage in the threads which can reduce the thread's holding power.

Threads in integral locking sleeves on syringes can be made with a greater height and more stability by unscrewing the syringe barrel and integral sleeve from its mold rather than using the longitudinal strip ejection process. However, such unscrewing process requires expensive mechanisms on the mold which substantially increase manufacturing cost.

SUMMARY OF THE INVENTION

The above problems with integral strip ejected locking sleeves in a thermoplastic sleeve have been overcome by the present invention. This invention includes screwing a needle hub with protruding ears partway into a locking sleeve, and thereafter longitudinally staking the hub to firmly seat it onto the tapered adapter and space the hub's projecting ears from a rear surface of the sleeve's threads. This relieves abutting stresses between the threads and hub ears, and also permits very firm assembly of the needle to the tapered adapter by the manufacturer without scarring the sleeve's threads.

THE DRAWINGS

DETAILED DESCRIPTION

Figure 1:
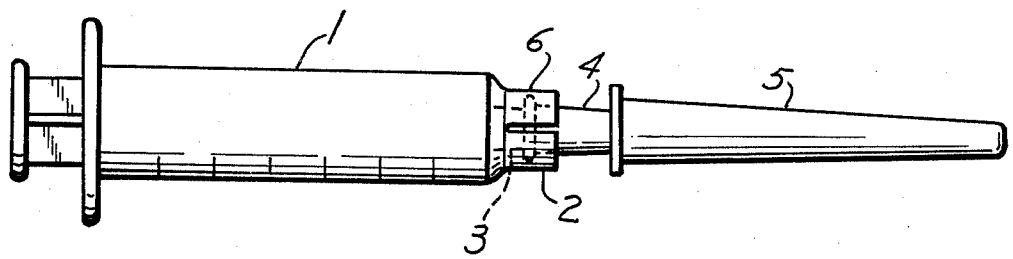
FIG. 1 is a side elevational view of the syringe with attached needle.

In FIG. 1, a syringe barrel 1 has an internally threaded locking sleeve 2 surrounding a tapered adapter 3 to which is mounted a needle hub 4. Needle hub 4 is connected to a conventional cannula (not shown) which is encased inside a protector 5. Preferably, locking sleeve 2 has several longitudinal slots 6 to aid in strip ejection of thermoplastic sleeve 2 which is integrally formed with barrel 1.

Figure 2:
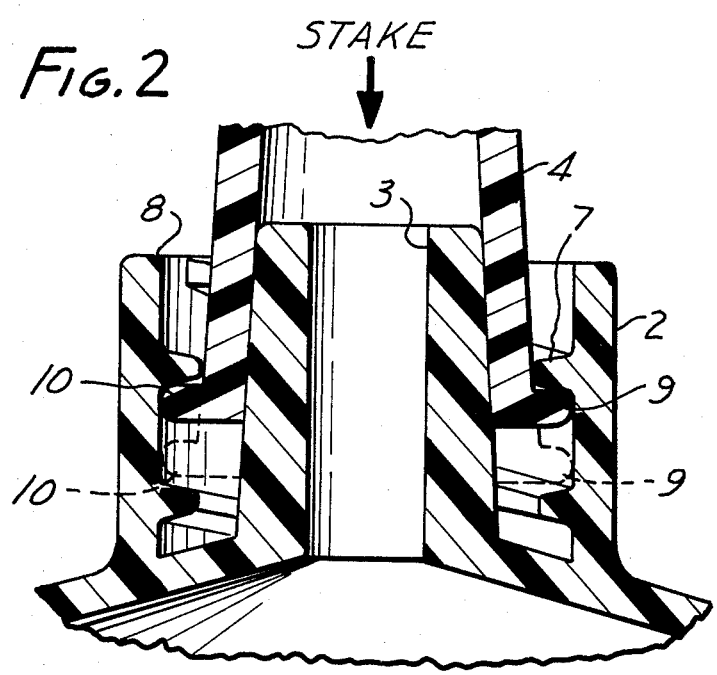
FIG. 2 is an enlarged fragmentary sectional view of a forward upstanding tip of a syringe barrel showing assembly of a needle hub.

The relationship of needle hub 4 and sleeve 2 are best seen in FIG. 2. Here the internal threads, represented as 7, are preferably in double helical form in that the sleeve has two spiral threads each having its own lead-in entrance adjacent a forward portion 8 of the sleeve. These two lead-ins are diametrically opposed on opposite sides of the sleeve 2.

Because of the longitudinal strip ejection of the integral thread 7, its size and rear surface slope structure are limited to permit the strip ejection without scarring or damaging thread 7. In a first step of the assembly process, hub 4 is screwed into sleeve 2 until it begins to wedge unto tapered adapter 3. An assembly machine performing this screw on step is adjusted so that its screwing motion is not so forceful as to snap ears 9 and 10 on the hub out from behind threads 7. Thus, during this step no damage is done to thread 7.

After the partial assembly by screwing, a second step of longitudinal staking is accomplished. This involves applying a force of at least 10 pounds axial force to firmly wedge the hub 4 onto tapered adapter 3. This staking is done without a screwing motion and causes ears 9 and 10 to assume the positions shown in dotted line. This relieves any abutment pressure between the hub ears and threads during storage.

Figure 3:
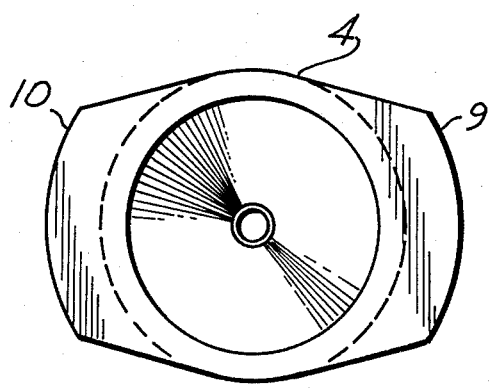
FIG. 3 is a rear end view of the needle hub showing its projecting ears.
Figure 4:
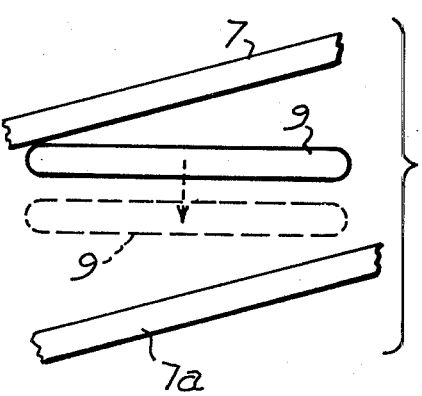
FIG. 4 is a fragmentary schematic view showing the vertical positioning of the hub ear between adjacent threads.

FIG. 3 shows a rear end view of the needle hub 4 with its protruding ears 9 and 10 that have a considerable width for gripping the sleeve threads over a wide area. The ear width is shown in FIG. 3. The relationship between adjoining threads and ear width is shown schematically in FIG. 4. Here thread sections 7 and 7a are longitudinally separated by a distance sufficient to permit longitudinal staking to a position shown in dotted line without substantial damage to thread section 7a. For the schematic illustration, thread sections 7 and 7a are not shown in spiral form as they would be on an internal surface of sleeve 2.

The above process for assembling the needle and syringe and its resulting structure works very well when a double helical thread has approximately 8 simulate threads/inch. For purposes of determining this thread pitch, both helical threads are included.

Even though the needle assembled by the above screwing and subsequent staking process very firmly attaches the needle to the syringe in the position shown by dotted line, a nurse or physician can readily remove the needle by a twisting motion for changing needle size, etc., when desired.

In the foregoing description, a specific example has been used to describe the invention. However, it is understood by those skilled in the art that certain modifications can be made to this example without departing from the spirit and scope of the invention.

I claim:

1. A syringe and attached needle hub in which the syringe has a tapered adapter surrounded by an internally threaded locking sleeve and the needle hub has at least one laterally protruding ear, wherein the improvement comprises: a longitudinal spacing between a forward surface of the needle hub's ear and a longitudinally aligned rearward surface area of a thread on the sleeve, whereby abutting pressure between the thread and needle hub ear are relieved during storage.

2. A syringe and attached needle hub as set forth in claim 1, wherein the needle hub has a pair of diametrically opposed ears.

3. A syringe and attached needle hub as set forth in claim 1, wherein both the needle hub ears and locking sleeve threads are thermoplastic.

4. A syringe and attached needle hub as set forth in claim 1, wherein the locking sleeve has a double helic thread with approximately 8 simulate threads per inch based on both threads.

5. A method of assembling a needle hub with at least one laterally protruding ear to a syringe with a tapered adapter surrounded by an internally threaded locking sleeve, which includes the steps of:

(a) screwing the needle hub partway onto the adapter with the ear engaging the threads of the locking sleeves; and (b) longitudinally staking the needle hub to the syringe adapter to longitudinally separate a forward surface of the needle hub ear from a longitudinally aligned rearward surface of the sleeve's thread.

6. A method as set forth in claim 5, wherein the staking force is at least 10 pounds.

* * * * *